US008492312B2

(12) United States Patent
Thomas

(10) Patent No.: US 8,492,312 B2
(45) Date of Patent: Jul. 23, 2013

(54) SYSTEMIC PLANT CONDITIONING COMPOSITION

(75) Inventor: Levar E. Thomas, Duluth, MN (US)

(73) Assignee: Regents of the University of Minnestoa, St. Paul, MN (US)

( * ) Notice: Subject to any disclaimer, the term of this patent is extended or adjusted under 35 U.S.C. 154(b) by 1437 days.

(21) Appl. No.: 11/595,464

(22) Filed: Nov. 9, 2006

(65) Prior Publication Data

US 2007/0104751 A1 May 10, 2007

Related U.S. Application Data

(60) Provisional application No. 60/736,137, filed on Nov. 10, 2005.

(51) Int. Cl.
*A01N 37/18* (2006.01)

(52) U.S. Cl.
USPC .......................................... 504/334; 504/336

(58) Field of Classification Search
None
See application file for complete search history.

(56) References Cited

U.S. PATENT DOCUMENTS

| | | | | |
|---|---|---|---|---|
| 3,756,801 | A * | 9/1973 | Herschler et al. | 504/116.1 |
| 3,813,345 | A | 5/1974 | Urton | |
| 4,291,497 | A | 9/1981 | Manakov | |
| 4,356,934 | A | 11/1982 | Knake | |
| 4,596,206 | A | 6/1986 | Berge et al. | |
| 4,772,490 | A | 9/1988 | Kögler et al. | |
| 4,994,487 | A | 2/1991 | Haglund | |
| 5,525,597 | A * | 6/1996 | Hainrihar et al. | 514/75 |
| 5,527,366 | A | 6/1996 | Mazurkiewicz | |
| 5,575,224 | A | 11/1996 | Roger | |
| 5,597,778 | A | 1/1997 | Smale | |
| 5,922,649 | A * | 7/1999 | Pehu et al. | 504/320 |
| 6,011,061 | A | 1/2000 | Lai | |
| 6,720,170 | B2 * | 4/2004 | Hiromoto | 435/183 |
| 7,001,869 | B2 * | 2/2006 | Johnson | 504/100 |
| 2004/0234492 | A1 | 11/2004 | Stockel | |
| 2005/0239675 | A1 * | 10/2005 | Makansi | 510/223 |

FOREIGN PATENT DOCUMENTS

| | | | |
|---|---|---|---|
| WO | WO 96/41530 | | 12/1996 |
| WO | WO 9901032 | * | 1/1999 |
| WO | WO 00/45637 | * | 8/2000 |
| WO | WO02102148 | * | 12/2002 |
| WO | WO 2007/058874 A3 | | 5/2007 |

OTHER PUBLICATIONS

Greger M. et al., "Effects of Cd2+ and EDTA on young sugar beets (*Beta vulgaris*),I. Cd2+ uptake and sugar accumulation", *Physiologia Plantarum*, 66:69-74 (1986).
Quintero J. et al., "Glucose-induced activation of rubidium transport and water flux in sunflower root systems". *Journal of Experimental Botany*, 52:99-104 (2001).
International Search Report for International Publication No. WO 2007/058874 A3 (2007).
Appleton et al., "Trees and Shrubs that Tolerate Saline Soils and Salt Spray Drift", *Virginia Cooperative Extension*, Virginia Tech, http://pubs.ext.vt.edu/430/430-031/430-031.html, 5 pages, (2009).
Beckerman et al., "Salt Damage in Landscape Plants, ID-412-W", *Purdue Extension, Purdue Agriculture*, Purdue University, 1-11 (2009).
Brubaker, "Difference Between Ammonium Lauryl Sulfate and Sodium Lauryl Sulfate", http://www.ehow.com/facts_6147573_difference-sulfate-sodium-lauryl-sulfate.html, 4 pages, (Jul. 2006).
Gervais, et al, "Capsaicin Technical Fact Sheet", *National Pesticide Information Center*, Oregon State University Extension Services; http://npic.orst.edu/factsheets/Capsaicintech.pdf, 1-11 (2008).
Jacob et al., "Pharmacology of DMSO", *Department of Surgery*, Oregon Health Science University, Portland, Oregon, 97201; http://www.dmso.org/articles/information/pherschler.htm, 1-18 (1986).
University of Minnesota, "SULIS Sustainable Urban Landscape Information Series", http://www.sustland.umn.edu/maint/nutrition.html, 1-4 (2006).
Vagts, "Ammonia Fertilizer and Soil pH", *Iowa State University Extension*; http://www.extension.iastate.edu/nwcrops/fertilizer_and_soil_ph.htm, 3 pages (2005).
Engels et al., "Influence of the Form of Nitrogen Supply on Root Uptake and Translocation of Cations in the Xylem Exudate of Maize (*Zea mays* L.)", *Journal of Experimental Botany*, vol. 44, No. 268, 1695-1701, (1993).
Gronwald et al., "Effect of Ammonium Sulfate on Absorption of Imazethapyr by Quackgrass (*Elytrigia repens*) and Maize (*Zea mays*) Cell Suspension Cultures", *Weed Science*, vol. 41, 325-334 (1993).

* cited by examiner

*Primary Examiner* — Alton Pryor
(74) *Attorney, Agent, or Firm* — Viksnins Harris & Padys PLLP

(57) ABSTRACT

This invention relates to compositions and methods facilitating availability, uptake and translocation of active ingredients in plants. More specifically, this invention relates to the surprising discovery that the application to the roots, such as administration to the soil surrounding plants, of two or more osmolytes in combination with an active ingredient, either simultaneously or within a short time of each other, results in an induction of translocation of active ingredient from the roots systemically into the plant.

25 Claims, No Drawings

SYSTEMIC PLANT CONDITIONING COMPOSITION

This application claims priority under 35 U.S.C. 119(e) to provisional application U.S. Ser. No. 60/736,137, filed Nov. 10, 2005, which application is incorporated hereby by reference in its entirety.

1. FIELD OF THE INVENTION

This invention relates to compositions and methods facilitating availability, uptake and translocation of active ingredients in plants. More specifically, this invention relates to the surprising discovery that the application to the roots, such as administration to the soil surrounding plants, of two or more osmolytes in combination with an active ingredient, either simultaneously or within a short time of each other, results in an induction of translocation of active ingredient from the roots systemically into the plant.

2. BACKGROUND

Commercial cultivation of plants is a major part of the economy, encompassing not only crops grown for human food and animal feed, but also crops such as cotton grown for fiber, trees grown for lumber, and others, such as flowers grown for beauty. The importance of plants to people and to the economy can hardly be overstated. Plants are subject to constant attack by insects and other animals, fungi, bacteria, viruses, nematodes, and other pathogens. When pathogens find susceptible plants, these attacks can result in the loss of yield and quality, and may result in the loss of entire crops. These losses result in substantial economic harm to the growers and, in some areas of the world, contribute to famine.

There is an on-going need for a means of protecting a variety of trees, crops, flowers, decorative and other plants in the field from pests and pathogens more effectively, at lower cost, and with less effort than by the use of pesticides and other traditional chemical agents. Moreover, what is needed is a means of providing this protection with lower and less lasting damage to the environment than caused by such conventional agents.

Various devices and systems for the application of systemics to plants, seeds, and soil, have been developed in the art. U.S. Pat. No. 5,527,366 discloses a method of applying an herbicide to plants that includes delivering a liquid herbicide solution to the plant foliage in a pressurized jet stream to physically disrupt the surface of the foliage. U.S. Pat. No. 4,291,497 describes a method of introducing a chemical agent into plants by spraying or dipping the plant organs into the agent and allowing the agent to penetrate the plant system. U.S. Pat. Nos. 4,994,487 and 5,575,224 disclose a device for injecting a liquid pesticide (fungicide and herbicide, respectively) into the soil adjacent to the root system of plants. U.S. Pat. No. 4,356,934 discloses a seed treatment method that includes spraying of an emulsion containing an insecticide, fungicide or bactericide, onto the seed prior to planting. U.S. Pat. No. 4,596,206 discloses an apparatus for treatment of seeds with a liquid insecticide-fungicide, prior to planting.

3. SUMMARY OF THE INVENTION

The present invention provides novel compositions and methods of protecting plants from pests and pathogens.

Systemic Plant Protection (SPP) is the innovative combination of solvents and transport agents to facilitate availability, uptake and translocation of active ingredients for the purposes of plant protection. This technology addresses plant protection through a system level approach. Components include adjuvants and solvents that condition the soil-plant media, and subsequently the roots, to receive, absorb, transport and release functional ingredients to the systemic benefit of the plant. The use of this technology results in a safe, sustained and valued added benefit to the crop. Using the present technology, active ingredients are induced to be plant available that are otherwise limited or unavailable for the added benefit of plant protection.

The present invention can be used for browse deterrence, pest aversion, insect repellency, control of diseases, enhanced plant health and crop improvement. Active ingredients are assimilated into tissue and dispersed throughout the plant through natural cellular solutions to accomplish these functions. This technology can be used with nonfood crops such as reforestation seedlings, landscape materials, ornamentals, perennials, floral crops and other annuals not meant for human consumption. Additionally, in the case of crop improvement, additives for livestock and human nutrition (including pharmaceuticals) can be systemically induced.

SPP utilizes FDA approved ingredients as solvents and transport agents for sustained systemic functions and benefits. These products can be applied at the nursery level to transplants or integrated into the cultural management of crop in situ, for a residual benefit to the plants. The functional ingredients in SPP are used in personal care, cosmetic, and health care products. The technology is unique and versatile, in that active ingredients are induced to be plant available (i.e., absorbed and translocated systemically) that are fundamentally, naturally not assimilated by the target plant. SPP facilitates plant assimilation of the added benefit of sustained plant protection.

The existing/available technology results in the deployment of active ingredients as topical coating of limited duration and durability, thus often cost prohibitive due to the necessity of repeated applications. Also, SPP can be integrated into conventional irrigation systems and other cultural regimes, without loss of benefits. Such integration is most cost effective for commercial operations. Finally, SPP facilitates plant assimilation of active ingredients not otherwise plant available and functional.

The invention provides compositions for soil application to plants comprising an active ingredient composition and two or more osmolytic carrier compositions where the amount of the active ingredient is elevated over the level naturally found in an untreated plant. In addition to the active ingredient, the formulation may also include an adjuvant. As is known in the art, an adjuvant is used in a formulation to aid the operation or improve the effectiveness of the pesticide. The term "adjuvant" includes such materials, as wetting agents, spreaders, emulsifiers, dispersing agents, foaming adjuvants, foam suppressants, penetrants, thickeners, antifreeze agents, correctives, fillers and carriers.

The present invention provides methods of introducing an active ingredient into a plant by contacting one or more roots and root related structures (i.e., fine roots and root hairs) of a plant with an active ingredient composition and two or more (e.g., two, three, four, five, six, seven, eight, nine, ten, etc.) osmolytic carrier compositions, where the amount of the active ingredient is elevated over the level naturally found in an untreated plant. In certain embodiments, the active ingredient is elevated by at least 1% over the level naturally found in an untreated plant. In certain embodiments, the amount of active ingredient is elevated by 10%, 100%, 1000% or more over the level naturally found in an untreated plant.

In the present invention EDTA (ethylenediaminetetraacetic acid) can be used as a chelating adjuvant, DMSO (dimethyl sulfoxide) can be used as a solvent/osmolyte, ALS (ammonium laurel sulfate) can be used as a transport agent and surfactant, BABA (Beta aminobutyric acid) can be used as a plant growth hormone, and/or BTH (benzothiadiazole) can be used as a transport agent.

The present invention provides a systemic plant conditioning composition for conditioning a target plant that has an osmotic membrane, where the conditioning composition contains (a) an active ingredient, and (b) an osmolyte carrier composition, wherein the active ingredient is exogenous and wherein the osmolyte composition comprises at least two solutes where at least one solute is capable of translocating into and within a plant through the roots, and wherein at least one solute is capable of carrying the active ingredient into and within the plant. In certain embodiments, the conditioning composition may further contain a chelating agent (e.g., EDTA), and/or a surfactant or wetting agent (e.g., ammonium laurel sulfate (ALS)). In certain embodiments at least one solute is a sulfoxide (e.g., DMSO). Alternatively, at least one solute is betaine or glycine betaine. In certain embodiments, the conditioning composition further contains a solubilizing agent that will not burn the plant, such as ethanol or methanol.

In certain embodiments the active ingredient is a browse deterrent, a nutrient, an insecticide, or a fungicide. In certain embodiments, the browse deterrent is denatonium benzoate, capsaicin, putramine or proven antifeedants, aversion or feed refusal agents singularly or in combination. In certain embodiments, the feed refusal agent is vomitoxin. In certain embodiments the active ingredient is a nutrient, such as ammonia or other nitrogenous compound, phosphate, micronutrient or plant growth hormone of known and proven effectiveness. In certain embodiments the active ingredient is an insecticide, such as a synthesized or natural insecticide of known and proven effectiveness on any sucking, chewing and boring pests. In certain embodiments the active ingredient is a small molecule that is not indigenous (i.e., "exogenous") to the particular target plant, such as a vitamin, phytonutrient, medicinal, pharmaceutical, nutraceutical or other natural compound of known and proven health benefits. In certain embodiments the active ingredient is a fungicide, such as azoxystrobin, bordeaux, propiconazole, triadimefon, myclobutanil, thiophanate-methyl, boscalid, fenbuconazole, fenhexamid, fosetyl-al, iprodione, vinclozolin, chlorothalonil, cyprodinil, copper octanoate, daconil, triforine, captan, borax, benomyl, mancozeb, sulfur, maneb, aluminum tris, metalaxyl, Mefenoxam, propiconazole, thiram, fludioxonil, tebuconazole, carboxin, difenoconazol, or ziram. In certain embodiments the active ingredient provides systemic resistance to a pest or pathogen.

In certain embodiments, the active ingredient to osmolyte ratio is within the range of 10 ppm up to 1000 ppm (or any integer in between).

In certain embodiments, the osmolyte carrier composition contains three solutes.

In certain embodiments, the conditioning composition is formulated into a sustained release substance, which may include an encapsulated granule/prill or micro-encapsulated spheroid. In certain embodiments, the conditioning composition is formulated to provide sustained release of the active ingredients for a prescribed duration, such as thirty, sixty, ninety, one hundred twenty, or one hundred eighty days. In certain embodiments, the conditioning composition is formulated into a crystal, granule, liquid, solid, peat, organic fiber, prill, bead, soil additive, polymer, acrylamide, zeolite, silica, and/or clay.

The present invention further provides a delivery system that contains an osmolyte carrier composition, wherein the osmolyte composition comprises at least two solutes where at least one solute is capable of translocating into and within a plant through the roots, and wherein at least one solute is capable of carrying an active ingredient into and within the plant.

The present invention provides a method of administering a systemic plant conditioning composition for conditioning a target plant by delivering the composition to soil surrounding the roots of the plant. In certain embodiments the composition is not injected into the plant, nor is it topically administered to the plant. In certain embodiments, at least one osmolyte carrier conditions the osmotic membrane in the target plant for enhanced root uptake and translocation. In certain embodiments, the conditioning composition is formulated to provide sustained release of the active ingredients for a prescribed duration, such as thirty, sixty, ninety, one hundred twenty, or one hundred eighty days.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

4. DETAILED DESCRIPTION OF THE INVENTION

This invention arises from the surprising discovery that the application to plants of one or more active ingredient compositions and of two or more osmolytic carrier compositions, either simultaneously or within a short time of each other, results in an induction of translocation of active ingredient from the roots systemically into the plant.

This invention relates to formulations and methods for enhancing the efficacy of exogenous chemicals used in treating plants. An exogenous chemical, as defined herein, is any chemical substance, whether naturally or synthetically derived, which (a) has biological activity or is capable of releasing in a plant an ion, moiety or derivative which has biological activity, and (b) is applied to a plant with the intent or result that the chemical substance or its biologically active ion, moiety or derivative enter living cells or tissues of the plant and elicit a stimulatory, inhibitory, regulatory, therapeutic, toxic or lethal response in the plant itself or in a pathogen, parasite or feeding organism present in or on the plant. Examples of exogenous chemical substances include, but are not limited to, chemical pesticides (such as herbicides, algicides, fungicides, bactericides, viricides, insecticides, aphicides, miticides, nematicides, molluscicides, and the like), plant growth regulators, fertilizers and nutrients, gametocides, defoliants, desiccants, mixtures thereof, and the like. Other examples of exogenous chemical substance include, but are not limited to, nutritional additives, including vitamins and pharmaceuticals.

The term "combining" as used herein refers to the mingling of two or more liquid, solid or aerosolized components before, during or after contact to plants.

The phrase "increase the level above the level found in an untreated plant" specifies a level that is above the level naturally found in a plant. The level from which change is measured is the level of the active ingredient found in an untreated plant, plant part, or plant product of interest. Therefore, the phrase quoted above refers to any concentration of active ingredient that is above this level.

The terms "administering" and "contacting" plants with a chemical or compound, as used herein, generally comprehend causing the plant to come into proximity with an exogenous liquid or solid (such as a powder) form of the chemical or compound. They do not comprehend the injection of compounds or chemicals into individual leaves or into individual plants.

As used herein the term "plant" encompasses all forms and organs of a monocotyledonous or dicotyledonous plant, including but not limited to the seed, the seedling, and mature plant. The plant can be edible by humans or by animals, can be grown for lumber or fiber content (such as cotton), can be used for or processed to become a medicine or medicament, or can be for decorative, ornamental, or recreational use, such as turf grass, house plants, flowers, or landscaping or Christmas trees.

As used herein, the term "pathogen resistance" refers to the ability of a plant to lessen the development of disease symptoms after exposure to a plant, insect or microbe.

The term "foliar application" refers to the application of substances to the foliage, or above-ground portions, of plants, and especially application to the leaves of the plants. It is understood in the art that incidental amounts of substances used in foliar applications may filter to or contact the soil, but not in quantities that will permit penetration of the soil and significant contacting of the plant's roots compared to the amount contacting the leaves and other above-ground structures.

The term "soil application" refers to the application of a substance to the soil around a plant, where the intent is either to affect the soil directly or to place the roots of the plant in contact with the substance. Generally, substances applied through a soil application will not contact the foliage, but it is possible that incidental amounts of substances used in soil applications may contact the foliage in quantities which will not significant compared to the amount contacting the roots and other below-ground structures.

A. Systemic Plant Conditioning Compositions

1. Active Ingredients

Active ingredients that can be used in the present invention include chemicals, such as herbicides, insecticides, fungicides, bacteriocides, plant growth regulators and nutritional additives for crop improvement.

Examples of suitable fungicides are provided in Table 1 below.

TABLE 1

| Fungicides Reference: Cornell, EPA and Federal Register 2005 |
|---|
| acetic acid |
| aluminum-phosphine |
| anilazine (Dyrene) |
| ampelomyces quisqualis (AQ10) |
| azoxystrobin (Abound) |
| *bacillus licheniformis* SB3086 |
| *bacillus pumilus* GB34 |
| *bacillus pumilus* strain QST 2808 (SonataTM) |
| *bacillus subtilis* |
| *bacillus subtilis* MBI 600 |
| basic copper sulfate |
| benomyl (Benlate) |

TABLE 1-continued

| Fungicides Reference: Cornell, EPA and Federal Register 2005 |
|---|
| boscalid |
| biphenyl (diphenyl) |
| bordeaux |
| cadmium chloride |
| cadmium compounds |
| captafol (Difolatan) |
| captan |
| carbon disulfide |
| carboxin (Vitavax) |
| cedar (natural) pesticides |
| chloroneb (Demosan, Tersan-SP) |
| chlorothalonil (Bravo) |
| cinnamaldehyde |
| copper ammonium carbonate |
| copper compounds |
| copper-hydroxide (Kocide) |
| copper octanoate |
| copper oleate |
| cuprous, cupric oxide |
| cyazofamid |
| cycloheximide (Acti-dione) |
| cymoxanil |
| cyproconazole (Alto, Sentinel) |
| cyprodinil |
| dichlone (Phygon, Quintar) |
| dicloran (Botran) |
| difenoconazole (Score) |
| dimethomorph (Acrobat) |
| dinocap (Karathane) |
| dithianon (Delan) |
| dodemorph acetate (Milban) |
| dodine (Cyprex) |
| EBDCs (General Information) |
| etridiazole (Ethazol, Terrazole) |
| famoxadone |
| fenamidone (Reason) |
| fenaminosulf (Dexon) |
| fenamiphos (Nemacur) |
| fenarimol (Rubigan) |
| fenbuconazole |
| fentin hydroxide (Du-Ter, TPTH) |
| ferbam |
| fluazinam |
| fludioxonil (Maxim) |
| fluoxastrobin |
| flutolanil (Moncut) |
| fosetyl-al (Aliette) |
| gliocladium virens GL-21 (WRC-GL-21) |
| glyodin |
| hexachlorobenzene (HCB, Anticarie) |
| hexaconazole |
| imazalil (Fecundal, Fungaflor) |
| iprodione |
| iprovalicarb |
| kasugamycin |
| mancozeb (Dithane M-45, Manzate 200) |
| maneb (Dithane M-22, Manzate) |
| manganous dimethyldithiocarbamate (manam) |
| mercuric chloride (Calo-Gran) |
| metalaxyl (Apron, Ridomil, Subdue) |
| metiram (Polyram) |
| myclobutanil |
| nabam (Dithane A-40) |
| neem oil |
| oxadixyl |
| oxycarboxin (Plantvax) |
| oxytetracycline |
| oxythioquinox (Morestan) |
| paraformaldehyde |
| pentachloronitrobenzene (Terraclor) |
| pentachlorophenol |
| phosphorous acid |
| phosphorous acid (mono- and di-potassium salts) |
| polyoxin D zinc salt (Endorse WP Turf Fungicide) |

TABLE 1-continued

| Fungicides Reference: Cornell, EPA and Federal Register 2005 |
|---|
| potassium bicarbonate |
| procymidone (Sumilex) |
| propamocarb hydrochloride (Tattoo) |
| propiconazole (Tilt) |
| propiconazole + trifloxystrobin |
| pyraclostrobin |
| pyraclostrobin + boscalid |
| pyrimethanil |
| quinoxyfen |
| sodium bicarbonate |
| sodium carbonate peroxyhydrate |
| sodium diacetate |
| sodium propionate |
| streptomycin (Agri-Strep, Agrimycin) |
| sulfur (Kolospray, etc.) |
| TCMTB (Busan) |
| tebuconazole (Elite, Folicur) |
| terramycin (Myco shield) |
| tetraconazole |
| thiabendazole (Arbotect, Mertect) |
| thiophanate ethyl (Topsin, Cleary's 3336) |
| thiophanate-methyl (Topsin M) |
| thiram (Arasan, Tersan 75) |
| tolylfluanid (Euparen M) |
| triadimefon (Bayleton) |
| triadimenol (Baytan) |
| trichoderma (Binab T) |
| trichoderma harzianum (T-22G, F-Stop) |
| trifloxystrobin |
| triflumizole (Terraguard, Procure) |
| triforine (Funginex) |
| triphenyltin hydroxide (TPTH) |
| triticonazole |
| validamycin (Validacin) |
| vinclozolin (Ronilan) |
| *xanthomonas campestris* subsp. *vesicatoria* |
| zinc borate (Firebreak ZB) |
| zinc sulfate |
| zineb (Dithane Z-78, Parzate) |
| ziram (Milbam) |
| zoxamide |

Examples of suitable herbicides, growth regulators and desiccants are provided in Table 2 below.

TABLE 2

| Herbicides Growth Regulators and Desiccants Reference: Cornell, EPA and Federal Register 2005 |
|---|
| 2,4-D (Dacamine, Weed-B-Gon) |
| 2,4-DB (Butoxone, Butyrac) |
| 2,4-DP (dichlorprop) |
| 2,6-Diisopropylnaphthalene |
| 2,4 D-dimethylamine |
| 6-benzyladenine (Accel) |
| acetochlor (Harness) |
| acibenzolar-S-methyl |
| acifluorfen (Tackle) |
| acrolein (Aqualin, Magnacide) |
| alachlor (Lasso) |
| allidochlor (Randox) |
| ametryn (Evik) |
| amitrole (Amizol, Amino Triazole) |
| ammonium sulfamate (Ammate) |
| arsenic acid |
| asulam (Asulox) |
| atrazine (AAtrex, Atrazine) |
| auxin |
| aminoethoxyvinylglycine (AVG) |
| azafenidin |
| benefin (Balan, Balfin) |
| bensulfuron-methyl |
| bensulide (Betasan, Prefar) |

TABLE 2-continued

| Herbicides Growth Regulators and Desiccants Reference: Cornell, EPA and Federal Register 2005 |
|---|
| bentazon (Basagran) |
| borax |
| bromacil (Hyvar X, XL) |
| bromoxynil (Brominal, Buctril) |
| butylate (Sutan, Sutan+) |
| cacodylic acid |
| carfentrazone-ethyl |
| chloramben |
| chlorimuron ethyl (DPX F6025) |
| chloroxuron |
| chlorpropham |
| chlorsulfuron |
| cimectacarb |
| clethodim |
| clodinafop-propargyl |
| clofencet |
| clomazone |
| clopyralid |
| clopyralid, monoethanolamine |
| cloransulam-methyl (Firstrate) |
| copper chelate (Cutrine-Plus) |
| copper-ethylenediamine complex |
| copper sulfate (Bluestone) |
| corn gluten |
| cuprous chloride |
| cyanazine (Bladex) |
| cyclanilide |
| cycloate (Ro-Neet) |
| cymoxanil |
| cytokinin |
| dalapon (Dowpon, Revenge) |
| daminozide (Alar, B-Nine) |
| DCPA (Dacthal) |
| desmedipham (Betanex) |
| diallate (Avadex) |
| dicamba (Banvel) |
| dicamba salt |
| dichlobenil (Casoron) |
| dichlormid |
| dichlorprop (Weedone, Cornox) |
| diclofop methyl (Hoelon) |
| diclosulam |
| diethanolamine |
| diethatyl ethyl (Antor) |
| difenzoquat (Avenge) |
| diflufenzopyr |
| diglycolamine |
| dimethenamid (Frontier) |
| dimethenamid-P |
| dinoseb (Premerge, Dinitro) |
| diphenamid (Dymid, Enide) |
| diphenylamine |
| dipropetryn (Sancap) |
| diquat (Reglone, Aquacide) |
| dithiopyr (Dimension) |
| diuron (Karmex) |
| dodecylammonium |
| endothall (Aquathol, Hydrothol) |
| EPTC (Eptam) |
| ethalfluralin (Curbit, Sonalan) |
| ethametsulfuron-methyl (Muster) |
| ethephon (Ethrel, Florel) |
| ethylene |
| fatty alcohol |
| fenac (Fenatrol) |
| fenoprop (Silvex) |
| fenoxaprop-ethyl (Acclaim, Horizon) |
| fluazifop-butyl (Fusilade) |
| flucarbazone-sodium |
| fluchloralin (Basalin) |
| flufenacet |
| flumetsulam (Broadstrike) |
| flumiclorac pentyl ester |
| flumioxazin |
| fluometuron (Cotoran, Lanex) |
| fluridone (Sonar, Brake, Pride) |
| fluroxypyr 1-methylheptyl ester (Starane) |

TABLE 2-continued

| Herbicides Growth Regulators and Desiccants Reference: Cornell, EPA and Federal Register 2005 |
|---|
| flurprimidol (Cutless) |
| fluthiacet-methyl (action) |
| FOE 5043 |
| fomesafen (Reflex) |
| foramsulfuron |
| forchlorfenuron |
| fosamine ammonium (Krenite) |
| gibberellic acid |
| glufosinate-ammonium (Rely, Finale) |
| glutamic acid |
| glyphosate (Roundup) |
| halosulfuron-methyl |
| haloxyfop (Verdict) |
| hexazinone (Velpar) |
| iodosulfuron methyl sodium |
| imazamox (Raptor) |
| imazapic (Cadre) |
| imazapic-ammonium |
| imazapyr |
| imazapyr, isopropylamine salt |
| imazaquin (Scepter) |
| imazethapyr |
| irgarol (Irgarol) |
| isopropalin (Paarlan) |
| isoxaben (Gallery, Snapshot) |
| isoxadifen-ethyl (AE F122006) |
| isoxaflutole (Balance) |
| karbutilate (Tanzene, Tandex) |
| lactofen (Cobra) |
| linuron (Lorox) |
| lysophosphatidylethanolamine (LPE) |
| maleic hydrazide (Royal MH-30) |
| MCPA (Chiptox, Dow MCP) |
| mecoprop (Chipco Turf Herb. MCPP) |
| mefluidide (Embark) |
| mepiquat chloride (Mepichlor) |
| mesotrione |
| methazole (Probe) |
| 1-methylcyclopropene (1-MCP) |
| methyl 5-[[(4,6-dimethoxy-2-pyrimidinyl)amino] carbonylaminosulfonyl]-3-chloro-1-methyl-1-H-pyrazole-4-carboxylate |
| metobromuron |
| metolachlor (Dual) |
| S-metolachlor |
| metribuzin (Lexone, Sencor) |
| metsulfuron methyl (Escort) |
| molinate |
| monocarbamide (Enquik, WilThin) |
| monuron (Monurex, Telvar) |
| 1-naphthaleneacetic acid (NAA) |
| napropamide (Devrinol) |
| naptalam (Alanap) |
| nicosulfuron (Accent) |
| norflurazon (Zorial, Solicam) |
| N,N-diethyl-2-(4-methylbenzyloxy)ethylamine hydrochloride (PT 807-HCL) |
| octylammonium |
| oryzalin (Surflan, Ryzelan) |
| oxadiazon (Ronstar) |
| oxyfluorfen (Goal) |
| paclobutrazol (Clipper 50 WP) |
| paraquat |
| pebulate (Tillam) |
| pelargonic acid |
| pendimethalin (Prowl) |
| perfluidone (Destun) |
| phenmedipham (Betanal, Spin-Aid) |
| picloram (Tordon, Grazon) |
| plant extract 620 |
| primisulfuron-methyl (Beacon) |
| prodiamine (Barricade) |
| profluralin (Tolban) |
| prohexadione-calcium (viviful) |
| prometon (Pramitol) |
| prometryn (Caparol, Prometrex, Primatol Q) |
| pronamide (Kerb) |
| propachlor (Ramrod, Bexton) |
| propanil |
| propazine (Milocep, Milogard) |
| propham (Chem Hoe) |
| prosulfuron (Exceed) |
| pyraflufen-ethyl |
| pyrazon (Pyramin) |
| pyridate (Lentagran, Tough) |
| pyrithiobac-sodium |
| quinclorac |
| quizalofop-p-ethyl (Assure, Super) |
| rimsulfuron |
| sesone |
| sethoxydim (Poast) |
| siduron (Tupersan) |
| simazine (Princep) |
| sodium chlorate (Defol) |
| sulfentrazone (Authority) |
| sulfometuron-methyl (Oust) |
| sulfonium |
| sulfosate (touchdown) |
| tebuthiuron (Graslan, Spike) |
| terbacil (Sinbar) |
| terbutryn (Clarosan) |
| thiazopyr (Visor) |
| thifensulfuron methyl (Harmony Extra) |
| triallate (Avadex BW, Far-Go) |
| triasulfuron (Amber) |
| tribenuron methyl (Express) |
| trichloroacetic acid (TCA) |
| tralkoxydim |
| tribufos (DEF) |
| triclopyr (Garlon) |
| triethylamine triclopyr |
| trifluralin (Treflan) |
| triflusulfuron methyl (Pinnacle) |
| vernolate (Vernam) |

Examples of suitable insecticides and miticides are provided in Table 3 below.

TABLE 3

| Insecticides and Miticides Reference: Cornell, EPA, and Federal Register 2005 |
|---|
| abamectin (Agri-Mek) |
| AC 303, 630 2SC |
| acephate (Orthene) |
| acequinocyl |
| acetamiprid |
| aldicarb (Temik) |
| aldoxycarb (Standak) |
| allethrin (Pynamin) |
| allyl isothiocyanate |
| amitraz (Mitac) |
| anagrapha falcifera (celery looper) |
| arosurf MSF |
| aspon |
| avermectin (Agri-Mek, Affirm) |
| azadirachtin (Align, Margosan, Neem) |
| azinphos methyl (Guthion) |
| *bacillus popilliae* (Doom) |
| *bacillus sphaericus* (VectoLex) |
| *bacillus thuringiensis* (CryIA(b) Delta-Endotoxin) |
| *bacillus thurigiensis* Cry3Bb protein (Vector ZMIR13L) |
| *bacillus thuringiensis* (Dipel, Bt) |
| *bacillus thuringiensis* (var. aizawai) |
| *bacillus thuringiensis* (var. buibui) |
| *bacillus thuringiensis* (var. israelensis) |
| *bacillus thuringiensis* (var. kurstaki) |
| *bacillus thuringiensis* (tolworthi Cry9C protein) |
| *beauveria bassiana* (Naturalis-L strain) |
| bendiocarb (Ficam) |
| benzoic acid |
| bifenazate |

TABLE 3-continued

| Insecticides and Miticides<br>Reference: Cornell, EPA, and Federal Register 2005 |
| --- |
| benzyl alcohol |
| bifenthrin (Talstar, Biflex) |
| boric acid |
| bufencarb |
| buprofezin |
| cadusafos (Rugby, Apache) |
| calcium arsenate (Pencal, Security) |
| canola oil |
| carbaryl (Sevin) |
| carbofuran (Furadan) |
| carbon disulfide |
| carbophenothion (Trithion) |
| cedar (natural) pesticides |
| CheckMate MRB Pheromone |
| chlordane |
| chlordimeform (Galecron, Fundal) |
| chlorethoxyfos (fortress) |
| chlorfenapyr |
| chlorobenzilate |
| chlorpyrifos (Dursban, Lorsban) |
| chlorpyrifos-methyl |
| chlorpyrifos (Dursban, Lorsban) |
| citriodiol |
| clothianidin |
| codlure pheromone |
| coumaphos |
| crotoxyphos (Ciodrin, Ciovap) |
| crufomate (Ruelene) |
| cryolite (Kryocide) |
| cyfluthrin (Baythroid) |
| lambda-cyhalothrin (Karate, Force, Warrior) |
| cyhexatin (Plictran) |
| cypermethrin (Ammo, Cymbush) |
| cyromazine (Larvadex, Trigard) |
| DDT |
| deltamethrin (K-Obiol) |
| demeton (Systox) |
| diazinon (D.Z.N., Spectracide) |
| dichlorvos (DDVP, Vapona) |
| dicofol (Kelthane) |
| dicrotophos (Bidrin) |
| dieldrin (Dieldrite) |
| dienochlor (Pentac) |
| N,N-diethyl-m-toluamide (Deet) |
| diflubenzuron (Dimilin) |
| dihydroazadirachtin |
| dimethoate (Cygon) |
| dinotefuran |
| dioxathion (Delnav) |
| disulfoton (Di-Syston) |
| (E)-9-dodecenyl acetate, (Z)-9-dodecenyl acetate |
| emamectin benzoate |
| endosulfan (Thiodan) |
| endrin |
| EPN |
| esbiothrin |
| esfenvalerate (Asana) |
| ethion |
| ethyl butylacetylaminopropionate |
| ethofenprox |
| ethoprop (Mocap) |
| ethylan (Perthane) |
| etoxazole |
| famphur (Bo-Ana, Warbex) |
| fenitrothion |
| fenoxycarb |
| fenpropathrin |
| fenpyroximate |
| fensulfothion |
| fenthion |
| fenvalerate |
| fipronil |
| flonicamid |
| flucythrinate |
| fluvalinate |
| fonofos |
| formetanate HCL |

TABLE 3-continued

| Insecticides and Miticides<br>Reference: Cornell, EPA, and Federal Register 2005 |
| --- |
| formic acid |
| formothion |
| fosthiazate |
| heliothis zea NPV |
| hexaflumuron |
| hexakis |
| hexythiazox |
| hydramethylnon |
| hydrogen cyanide |
| hydroprene |
| imidacloprid |
| indoxacarb |
| inorganic arsenicals |
| isofenphos |
| *jojoba* oil |
| kinoprene |
| lead arsenate |
| linalool |
| lindane |
| malathion |
| metarhizium anisopliae strain ESF1 |
| methamidophos |
| methidathion |
| methiocarb |
| methomyl |
| methoprene |
| methoxychlor |
| methoxyfenozide |
| methyl parathion |
| mevinphos (Phosdrin) |
| MK-0244 |
| monocrotophos (Azodrin) |
| naled (Dibrom) |
| neem oil |
| nicotine (Black Leaf 40) |
| nithiazine |
| *nosema locustae* |
| novaluron |
| noviflumuron |
| oxamyl (Vydate) |
| oxydemeton-methyl (Metasystox-R) |
| oxypurinol |
| parathion (ethyl) |
| permethrin (Ambush, Pounce) |
| petroleum oils (Volck) |
| pheromones |
| phorate (Thimet) |
| phosalone (Zolone) |
| phosmet (Imidan, Prolate) |
| phosphamidon (Dimecron) |
| picaridin |
| piperonyl butoxide |
| pirimicarb (Pirimor) |
| pirimiphos-methyl (Actellic) |
| p-menthane-3,8-diol (Off) |
| profenofos (Curacron) |
| propargite (Omite, Comite) |
| propetamphos (Safrotin) |
| propoxur (Baygon) |
| pymetrozine |
| pyrethrins (Pyrenone) |
| pyridaben (Sanmite) |
| pyriproxyfen |
| resmethrin (SBP-1382) |
| ronnel (Ectoral, Korlan) |
| rotenone |
| ryania |
| salicylic acid |
| sodium arsenate |
| spinosad |
| spiromesifen |
| spodoptera exigua (Spod-X) |
| *streptomyces griseoviridis* (Mycostop) |
| sucrose octanoate |
| sulfluramid (GX-071) |
| sulfotepp (Bladafum, Plantfum) |
| sulfur (Magnetic 6) |

TABLE 3-continued

| Insecticides and Miticides<br>Reference: Cornell, EPA, and Federal Register 2005 |
|---|
| sulprofos |
| tebufenozide (Confirm) |
| tebupirimfos |
| temephos (Abate) |
| TEPP (Kilmite 40) |
| terbufos (Counter) |
| tetrachlorvinphos (Rabon, Gardona) |
| tetradifon (Tedion V-18) |
| thiacloprid |
| thiamethoxam |
| thiodicarb (Larvin) |
| thymol |
| tomato pinworm (TPW) insect pheromone |
| toxaphene |
| tralomethrin (Scout) |
| triazamate |
| trichlorfon (Dipterex, Dylox) |
| trimethacarb (Broot) |
| *xanthine* |

Examples of suitable miscellaneous pesticides (Antimicrobial, Attractants, Bactericide, Disinfectant, Macrofoulants, etc.) are provided in Table 4 below.

TABLE 4

| Miscellaneous Pesticides (Antimicrobial, Attractants, Bactericide, Disinfectant, Macrofoulants, etc.)<br>Reference: Cornell, EPA and Federal Register 2005 |
|---|
| acrylic acid terpolymer |
| alpha-alkyl(C21–C71)-omega-hydroxypoly (oxyethylene) |
| alpha-alkyl(C21–C71)-omicron-hydroxypoly (oxyethylene) |
| ammonium bicarbonate |
| arsenic acid |
| benoxacor |
| biochemical floral attractants |
| brominated salicylanide (Temasept IV) |
| 2-bromo-2-nitro-1,3-propanediol |
| bronopol (Myacide B10) |
| calcium-hypochlorite |
| CAS Reg. No. 64359-81-5 |
| cellulose acetate |
| cetyl alcohol |
| chlorhexidine diacetate |
| chloroform et al. |
| cloquintocet-mexyl |
| creosote |
| crezasin |
| cucurbitacins |
| dantochlor |
| 4-(dichloroacetyl)-1-oxa-4-azospiro [4.5] decane (MON 4660) |
| didecyl dimethyl ammonium chloride |
| diethylene glycol |
| diphenylamine |
| epichlorohydrin |
| 1,2-ethanediamine |
| ethoxylated propoxylated (C12–C15) alcohols |
| ethyl-maltol |
| ethyl methylphenylglycidate |
| ethylene dichloride |
| fatty acids (amm.salts) |
| fatty acids (pot.salts) |
| fatty acids (Tall-Oil) |
| FD&C RED NO. 40 |
| furilazole |
| gellan gum |
| geraniol |
| glycolic acid |
| glycoserve |
| hexane |
| humic acid, sodium salt |
| hydrogen peroxide |
| hydroxyethylidene-1,1-diphosphonic acid (HEDP) |
| inorganic arsenicals |

TABLE 4-continued

| Miscellaneous Pesticides (Antimicrobial, Attractants, Bactericide, Disinfectant, Macrofoulants, etc.)<br>Reference: Cornell, EPA and Federal Register 2005 |
|---|
| *jojoba* oil |
| kaolin clay |
| L(+) lactic acid |
| lepidopteran pheromones |
| Limonene |
| m-cresol (Gallex) |
| mefenpyr-diethyl (HOE-107892) |
| metaldehyde (Meta, Metason) |
| methyl chloride |
| MON 13900 |
| nitrapyrin (N-Serve) |
| o-phenylphenol (Dowicide 1) |
| OBPA |
| octadecanoic acid |
| octanal |
| oleyl alcohol |
| oxazolidine E (Bioban CS-1246) |
| oxidized pine lignin |
| pentaerythritol stearates |
| perchloroethylene |
| pigments |
| poly (hexamethylene biguanide) hydrochloride |
| polymers/copolymers |
| potassium bromide |
| potassium citrate |
| potassium oleate |
| potassium permanganate |
| 2-propene-1-sulfonic acid |
| propylene oxide |
| silver sodium hydrogen zirconium phosphate (Antimicrobial AlphaSan ® RC 5000) |
| sodium/calcium hypochlorite (Clorox, bleach) |
| sodium hydroxymethylglycinate (Integra ® 44) |
| sodium omadine |
| sodium pentachlorophenate (Penta) |
| styrene-2-ethylhexyl acrylate-glycidyl |
| tetrakis (hydroxymethyl) phosphonium sulphate (THPS) |
| 1,1,1,2-tetrafluoroethane |
| titanium dioxide |
| tributyltin (TBT) |
| trimethylopropane |
| urea |
| urea-formaldehyde |
| vinyl acetate-ethylene |
| water soluble film inserts |
| xanthan gum - modified |
| zinc pyrithione |

Examples of suitable Rodenticides, Repellents, and Vertebrate Pesticides are provided in Table 5 below.

TABLE 5

| Rodenticides, Repellents, and Vertebrate Pesticides<br>Reference: Cornell, EPA and Federal Register 2005 |
|---|
| allyl isothiocyanate |
| 4-aminopyridine (Avitrol) |
| anthraquinone |
| antu (Anturat, Krysid) |
| azocosterol (Ornitrol) |
| benzaldehyde |
| black pepper |
| bone oil (Magic Circle) |
| brodifacoum (Talon, Havoc) |
| bromadiolone (Bromone, Maki) |
| capsaicin |
| cedar (natural) pesticides |
| 3-chloro-4-methylbenzenamine hydrochloride (Starlicide) |
| chlorophacinone (Rozol) |
| cholecalciferol (Vitamin D3) |
| difethialone (Generation) |
| diphacinone (Ramik, Promar) |
| denatonium benzoate (Bitrex) |

TABLE 5-continued

| Rodenticides, Repellents, and Vertebrate Pesticides Reference: Cornell, EPA and Federal Register 2005 |
|---|
| EPIBLOC |
| meat meal and red pepper |
| methyl anthranilate |
| naphthalene |
| n-butyl mercaptan (Scoot Deer) |
| paradichlorobenzene (PDB) |
| pindone (Pival, Pivalyn) |
| piperine |
| scilliroside (Red Squill, Rodine) |
| sodium fluoroacetate (1080) |
| strychnine (Nux Vomica) |
| strychnine sulfate |
| sulfaquinoxaline |
| warfarin (d-Con, Rodex) |
| zinc phosphide (Phosvin, KP) |

2. Osmolytic Carrier Compositions

Fundamentally, the present technology optimizes root absorption/uptake and vascular distribution of beneficial substances. In the present invention DMSO (dimethyl sulfoxide) can be used as a solvent/osmolyte. In certain embodiments, DMSO will be essential. EDTA (ethylenediaminetetraacetic acid) can be used as a chelating adjuvant. EDTA is especially effective in the presence of substances of metallic ion composition. ALS (ammonium laurel sulfate) can be used as a transport agent and surfactant. ALS can have the dual role of surfactant and transport function associated with the ammonium ion and its oxidized forms. BABA (Beta aminobutyric acid) can be used as a plant growth hormone, and/or BTH (benzothiadiazole) can be used as a transport agent. BABA and BTH are demonstrated and known to be effective and versatile on a wide size range of molecules.

Essentially, the soil particles and roots are conditioned by ALS so that the root structures are optimally exposed to the concentrated solution. BABA and BTH stimulate the physiological function of the root system. DMSO carries the active ingredients across the osmotic membrane of the roots and vascular cell walls, resulting in the systemic distribution of the active ingredients acropetally.

3. Inert Ingredients

Inert ingredients may include semi-permeable coatings, bulking agents and fillers. For example, the ingredients of this technology can be engineered for sustained release, i.e., combined with clay, formed into granules, enveloped in a polymer. The ingredients of this technology can be encapsulated or micro-encapsulated on a wide size range. Inert ingredients are those substances which are used to bulk, solidify, encapsulate or allow sustained delivery of the active ingredients.

One of ordinary skill in the art will understand that other inert ingredients may be included in all embodiments of the biologically active formulation of the invention to provide a more satisfactory formulation, provided the inert ingredients do not detract from the effect of the essential components of the invention. The composition may further contain other agents that either enhance the activity of the active ingredient or osmolyte carrier composition or complement their activity. Such additional factors and/or agents may be included in the composition to produce a synergistic effect, or to minimize side effects. The composition may further comprise fillers, salts, buffers, stabilizers, solubilizers, and other materials well known in the art.

It will be apparent to one of ordinary skill in the art that the "effective amount" of the active ingredient compound in a plant will be largely variable, depending on many factors, including the species of plant and its growth stage, row and plant spacing, environmental conditions, weather, etc. In certain embodiments, the active ingredient concentration is between about 0.01 to 10.0% (e.g., 0.01, 0.05, 0.1, 0.2, 1 0.3, 0.4, 0.5 0.6, 0.7, 0.8, 0.9, 1.0, 2.0, 3.0, 4.0, 5.0, 6.0, 7.0, 8.0, 9.0, or 10.0 or any integer or fraction in between), and the osmolyte carrier composition concentration is about also 0.01 to 10.0% (e.g., 0.01, 0.05, 0.1, 0.2, 1 0.3, 0.4, 0.5 0.6, 0.7, 0.8, 0.9, 1.0, 2.0, 3.0, 4.0, 5.0, 6.0, 7.0, 8.0, 9.0, or 10.0 or any integer or fraction in between), that is, the active ingredient is applied at about one-tenth the concentration of the osmolyte carrier composition.

An effective amount of active ingredient compound is an amount sufficient to induce a biological response in the plant, such that the level of active ingredient in the treated plant is greater than the levels of active ingredient in control (untreated) plants. Such amounts can be determined by routine testing. The effective amount can be achieved by one application of the composition. Alternatively, the effective amount is achieved by multiple applications of the composition to the plant. The amount of the active ingredient in the composition will depend upon the particular compound or mixture of compounds being employed, the plant tissue being treated, and the ability of the plant to take up the composition. For instance, young plants take up most compositions more readily than older plants. It is contemplated that the various compositions used to practice the method of the present invention should contain from about 0.01% to 10.0% active ingredients dependent on the resultant dilution ratio upon deployment. In certain embodiments, SPP should be considered a customized deployment and a "test case" should be conducted prior to commercial application over a large population. In certain embodiments, direct-to-crop application rates are most effective in the 1.0% to 2.0% range.

Generally, it is anticipated that cost and other considerations will lead the practitioner to apply the compositions at concentrations within this range. In some instances, a practitioner may, however, desire to apply the compositions at a higher concentration. There will be an upper limit on the concentration of different active ingredients that can be applied to a plant without toxicity, and the upper limit varies for different types of plants. Active ingredients must be used within the rate range listed on the product label, to not violate safety, environmental or product warranty. In most cases the lowest label rate will be effective with SPP. The size of the individual plant or the field density of the crop will dictate the volume of SPP mixture applied, as well as the concentration of active ingredient. Liquid concentrations of SPP can be applied through irrigation systems to greenhouse or field crops. In the case of deployment through irrigation, the concentration of active ingredient must be adjusted based on the rate of flow through the system. The use of SPP is customized for the application system and crop condition. For example, a concentration of 10% active ingredient with commensurate carriers can be deployed through an irrigation system at the rate of 25 gallons per minute for very effective coverage and results on containerized tree seedlings grown in a greenhouse.

The upper limit on the concentration of the active ingredients for any particular plant type can be routinely determined by any of several methods known in the art, such as exposing sample plants of the type in question to various concentrations of active ingredients and examining the plants for signs of stress, such as browning of tips of leaves, indicating that the concentration at which the stress signs occurred is too high for that type of plant. Upper limits on the concentration of osmolyte carrier composition can be determined in the same manner.

B. Administration of Systemic Plant Conditioning Compositions

In certain embodiments, the active ingredient and the osmolytic carrier composition will be applied together as a mixture, such as an aqueous solution or formulated granules. One example of granules is found in U.S. Pat. No. 4,772,490. Alternatively, the active ingredient and the osmolytic carrier composition will be administered within 36 hours of one another, within 24 hours of one another, within 12 hours or less of one another, or within about an hour of each other. In certain embodiments, pressurized or passive injection into the vascular system of the plant may not be recommended due to cost. Topical absorption through foliage and cuticle may be more cost effective.

The composition of the present invention is mixed thoroughly, and in the case of a liquid, the active ingredient is fully dissolved. The composition may be applied concurrently or sequentially (in any desired sequence) so long as each component performs as intended in accordance with the invention. If applied sequentially, the individual components may be applied over a short or long time frame.

The treatment of the plant may also involve adding the composition to the water supply of the plants. The application can be repeated as often as considered useful, with one or more "booster" applications applied to bolster resistance should the previously induced resistance begin to fade, as evidenced by the onset of disease symptoms. Thus, the formulation may be considered "prophylactic" as well as "therapeutic."

In certain soil application embodiments, the soil is first saturated to wet the particles of the soil so that the active ingredient/osmolyte mixture can move freely in the soil and reach the roots of the plants. Therefore, the soil is saturated to 70-80% field capacity with ordinary water prior to active ingredient/osmolyte application. The active ingredient/osmolyte mixture is then applied at a concentration of between 1 and about 100,000 ppm. Typically, the concentration will be between about 500 ppm and about 10,000 ppm, at a concentration of about 750 ppm to about 7,500 ppm, or at a concentration of about 800 ppm to about 5,000 ppm. The particular concentration to be chosen varies primarily according to the flow rate of water permitted by the method of application. Methods having a higher flow rate generally require a lower concentration of active ingredient/osmolyte mixture, perhaps because more water containing the mixture reaches the roots of the plants. Conversely, lower flow rates will generally require higher concentrations of active ingredient/osmolyte mixture. Alternatively, the time of the application of the mixture can be altered. Thus, use of a low flow rate and low concentration of mixture can be balanced by increasing the time in which the water containing the mixture is applied. Thus, halving the flow rate or concentration of mixture can be compensated for by doubling the application time of the water-mixture solution. While flow rate is a particularly important variable, the crop to which the mixture is being applied may also help determine the concentration of mixture to be applied. Typically, perennials take higher concentrations than do annuals.

It should be noted that the grower is usually well aware of the flow rate per acre of the irrigation or other soil application system in place on his or her property, as well as the acreage to be covered. The grower can calculate the amount of water that will be used in watering the land for any particular amount of time (for example, 300 gallons per minute times 50 acres times 30 minutes is 450,000 gallons of water). The grower can then calculate how much active ingredient/osmolyte mixture is needed to result in an application of the desired concentration of the mixture.

The active ingredient/osmolyte mixture is applied for a period of time, typically ranging from about two minutes to about an hour. In some cases, the practitioner may want to apply the mixture at a lower concentration, but for a longer period, such as overnight or over several days. Such applications are within the purview of the invention, so long as they result in increases in disease resistance (or other target biological activity). The time of the application will also vary according to the particular method employed. For drip systems, the mixture is applied for about 5 minutes to about 45 minutes. In certain embodiments, the mixture is applied for about 9 minutes to about 30 minutes, or the mixture can be applied for about 15 to about 25 minutes.

The active ingredient/osmolyte mixtures are typically applied to the soil by being run through a hose, pipe, drip, sprinkler, irrigation channel, or other mechanism. In practice, the devices used are not necessarily precision equipment. Accordingly, when the water flow is turned off, water will typically continue to drip or run from the hose or through the irrigation channel or other applicator for some time. It is therefore understood that the times of application will generally be an approximation and will be measured from the start of the flow of the mixture to when the flow of the mixture is turned off, whether or not some of the mixture continues to drip or run from the applicator.

Various liquid administration techniques can be used in different embodiments. One embodiment of a liquid administration technique is a drench/dip method. This method is designed for containerized seedlings and propagules. Root mass is immersed in SPP mixture to ensure thorough hydration of the medium. Saturated medium facilitates exposure and uptake by the seedling. These methods are useful for greenhouse crops and potted nursery plants. Another liquid technique is the use of a wettable powder. This method is designed for ingredients that are suspended in solution (i.e., not solubilized in the solvent components). Wettable powders are used for persistent drenches and topical applications for higher residence time. These methods are useful for landscape materials in place and orchards. Another liquid technique is the use of foliar spray. This method is designed for topical coating of foliage and above ground plant parts, and is often dual purpose (i.e., topical coating with over-spray penetrating through root uptake). This method requires leaf and cuticle penetration, and must be specifically formulated to accommodate surface coating. These methods are useful for exterior landscape environments. A fourth liquid technique is soil applied spray. This method is designed for exclusively for root uptake, and primarily for field use. Concentrate is specifically formulated for broadcast spray, soil penetration, high residence/duration and ease of uptake. These methods are useful for plantations (Christmas trees, for instance), orchards and fields. A fifth liquid technique is irrigation. This method is designed for greenhouse and controlled landscapes where irrigation systems are required. SPP product is metered into the water system and dose applied, repeatedly as necessary (i.e., application can be monitored). These methods are useful for greenhouse seedlings, turf and high value crops.

Alternatively, or additionally, the active ingredient/osmolyte mixture may be administered in the form of granules, in peat, etc. to the soil surrounding the roots of the target plant. In one embodiment, the active ingredient/osmolyte mixture is a solid (for instance, a powder or dust). These types of formulations as designed for static coating of crop. The powder form of this SPP product can be mixed with diatomaceous earth and other bioinsecticide products such at Bt for multiple benefits. These methods are useful for rose bushes and bedding plants with multiple pest problems. In another embodiment, the active ingredient/osmolyte mixture is granular (uncoated). These types of formulations are designed for immediate release and/or repeated applications. The SPP granular is soil applied. These methods are useful for soil borne insect control and/or, weed control (SPP delivers herbicide). In another embodiment, the active ingredient/osmolyte mixture is an impregnated matrix, such as a "saturated sponge" for sustained release. The SPP is held within a matrix structure, allowing physical solubility to be controlled and sustained. Examples of such matrices include peat or wood fiber as bulking agent for field application of SPP.

Alternatively, or additionally, the active ingredient/osmolyte mixture is administered in an encapsulated form. In one embodiment, the active ingredient/osmolyte mixture is micro-encapsulated. These formulations are designed for gel or viscous liquid concentrates of SPP. Examples include polymer coated liquid for sustained release. These methods are useful for high value crops and expensive active ingredients, such as nutritional enhancement of crop (e.g., folate and Vitamin A enriched healthy food crops to reduce spina bifida and vision related diseases in third world populations.) In another embodiment, the active ingredient/osmolyte mixture may be poly-coated. These formulations are designed for sustained release granules of SPP. Examples include polymer coated prills for high value applications. These formulations are similar to Osmocote, but for more expensive active ingredients. These methods are useful for, e.g., containerized tree seedling media packed with browse control ingredients in the greenhouse, which would provide sustained benefit after transplanting. In another embodiment, the active ingredient/osmolyte mixture is starch coated. These formulations are designed as an alternative to poly-coating. This granular formulation is appealing to natural growers. It accomplishes sustained release without the negative connotation of "plastic" coating.

Following application of the active ingredient/osmolyte mixture as set forth above, the mixture will typically be in the top few inches of soil. For many plants, the root system is deeper in the soil. It is therefore desirable to help move the mixture 6 to 12 inches into the soil to reach the root structures involved in active uptake. To achieve this, it is desirable to use a "water push" to create a concentration gradient after application of the active ingredient/osmolyte mixture. This is achieved by following the application of the active ingredient/osmolyte mixture with an application of water. The water application can be as short as a few minutes or as long as several hours. In certain embodiments, the water application is between about 30 minutes and about 1.5 hours, such as about one hour. Such "water pushes" to create concentration gradients are commonly used by farmers in applying agricultural chemicals and are accordingly well known in the art.

C. Uses of the Invention

The invention can be used to protect almost any plant capable of responding to pest or pathogenic attack with systemic acquired resistance. Assays for determining whether a particular type of plant can benefit from the induction of systemic acquired resistance by means of the invention are well known in the art. For example, insect population can be monitored through the use of sticky traps, examination of foliage and presence/absence of eggs/larvae. SPP offers a proactive approach to crop management. The active ingredient for a specific pest on the crop can be induced systemically to avoid initial infestation. Also, crops can be pre-treated in the nursery prior to field deployment to ensure complete protection.

The plants to be protected by means of the invention can be dicots, such as carrots, lettuce, tomatoes, grapes, citrus fruits, and beans, or monocots, such as corn. The plants can be grown for human or animal consumption, such as grains, vegetables, and fruits can be intended for decorative use, such as flowers, or can be intended for ornamental use, such as trees grown for use as lumber, ornamental trees, Christmas trees or plants intended for use as house plants. Further, they can be plants grown for fiber, such as cotton plants, for use as turf, for example on golf courses, lawns or ballfields, or for use as or in medicaments. Most commonly, the invention will be used to protect plants grown in fields as crops or in other open conditions, such as tree farms or turf, the invention can, however, also be used to protect plants grown in settings such as greenhouses and hothouses.

The invention can be used to protect plants against any pest or pathogen against which systemic acquired resistance can be generated. The Example demonstrate the use of the invention to protect trees against pests.

Non-limiting examples of plant pathogens include insects (e.g., *diptera, hymenoptera, coleoptera, lepidoptera, orthoptera, hemiptera*, and *homoptera*), bacteria (in soybeans, for example, *Pseudomonas syringae* pv. *glycinea* and *Xanthomonas campestris* pv. *phaseoli*), viruses (in soybeans, for example, Bean Pod Mottle Virus, Cowpea Chlorotic Mottle Virus, Peanut Mottle Virus, Soybean Dwarf Virus, Soybean Mosaic Virus, Tobacco Ringspot Virus, Tobacco Streak Virus, Bean Yellow Mosaic Virus, Black Gram Mottle Virus, Cowpea Mild Mottle Virus, Cowpea Severe Mosaic Virus, Indonesian Soybean Dwarf Virus, Mung Bean Yellow Mosaic Virus, Peanut Stripe Virus, Soybean Chlorotic Mottle Virus, Soybean Crinkle Leaf Virus, Soybean Yellow Vein Virus, and Tobacco Mosaic Virus), fungi (in soybeans, for example, *Cercospora sojina, Chaetomium cupreum, Colletotrichum truncatum*, Diaporthe-Phomopsis Complex, *Fusarium* spp., *Macrophomina phaseolina, Peronospora manschurica*), and nematodes (in soybeans, for example, Soybean Cyst Nematode, Lance Nematodes, Lesion Nematodes, Reniform Nematode, Root-Knot Nematodes, and Sting Nematodes).

Non-limiting examples of plant diseases include 1) infectious diseases such as a) bacterial diseases (in soybeans, for example, Bacterial Blight, Bacterial Pustule, Bacterial Tan Spot, Wildfire, Bacterial Wilts, and Crown Gall), b) mycoplasmalike diseases (in soybeans, for example, Machismo, Bud Proliferation, Witches' Broom and Phyllody), c) fungal diseases of foliage, upper stems, pods, and seeds (in soybeans, for example, *Alternaria* Leaf Spot and Pod Necrosis, Anthracnose, Brown Spot, *Cercospora* Blight and Leaf Spot, *Choanephora* Leaf Blight, Downy Mildew, Frogeye Leaf Spot, Phyllosticta Leaf Spot, Powdery Mildew, Red Leaf Blotch, Rhizoctonia Aerial Blight, Rust, Scab, and Target Spot), d) fungal diseases of roots and lower stems (in soybeans, for example, Brown Stem Rot, Charcoal Rot, *Fusarium* Blight or Wilt, Root Rot, and Pod and Collar Rot, *Phytophthora* Stem Rot, Pod and Stem Blight and Phomopsis Seed Decay, Stem Canker, *Pythium* Rot, Red Crown Rot, Rhizoctonia Diseases, *Sclerotinia* Stem Rot, *Sclerotium* Blight, and Thielaviopsis Root Rot), e) viral disease (in soybeans, for example, bud blight, soybean mosaic, f) nematode diseases, g) seedbome bacteria and bacterial diseases of seeds (in soybeans, for example, *Bacillus* Seed Decay), h) seedbome fungi and fungal diseases of seeds (in soybeans, for example, *Alternaria* Pod and Seed Decay, Purple Seed Stain, Yeast Spot (*Nematospora* Spot), and Phomopsis Seed Decay), i) seedborne viruses; 2) diseases of unknown or uncertain cause (in soybeans, for example, Foliage Blight, Sudden Death Syndrome, and Yellow Leaf Spot); and 3)

noninfectious or stress diseases (e.g., crusting and compaction, frost, hail, heat canker, lightning, sunburn, water stress, mineral deficiencies and toxicities, herbicide damage, insecticide damage, and air pollutants). Specific examples of administration would be for control of *phytophthora* root rot, *sclerotinia* white mold, brown stem rot and the soybean cyst nematode.

Because the invention protects plants against at least a portion of the damage that would otherwise be caused by these pests, a higher percentage of the plants grown for can be sold as first quality plants. Moreover, since less of the crop is unmarketable, the invention results in a higher yield per acre. These factors combine to result in higher revenues per acre for the grower.

D. Methods for Determining Effectiveness of Active Ingredient/Osmolyte Carrier Compositions in Plants In addition to crop monitoring for qualitative and/or anecdotal benefits, the tissue of the crop can be sampled and analyzed for the presence of the active ingredient. The baseline signature of the active ingredient is quantitatively establishment from a chemical standard. The tissue of the crop is collected from stem and foliage. This tissue is prepared for analysis by the method used on the standard. The concentration of the active ingredient is compared to the signature of the standard to quantify the presence of the compound in the crop. The analytical protocol is specific to the active ingredient. Repeated residue analysis over time can be used to quantify the duration of benefits. In many cases the method of analyses is HPLC (High Performance Liquid Chromatography).

The following examples are merely illustrative of aspects of the invention and are not to be construed as limiting in any way.

Example 1

Browse Control

The desired result of this example is control of browsing by deer on red pine tree seedlings through the application of Systemic Browse Deterrent (SBD). Containerized tree seedlings were treated in a nursery greenhouse with a solution of active ingredient (specifically 10% denatonium benzoate) combined in the SPP formulation of solvents and carriers (SBD-2 10× Concentrated Formulation: 44.6 grams denatonium benzoate as active ingredient, 8.0 ml of DMSO, 36 grams EDTA, 12 grams betaine and 20 ml of ammonium lauryl sulfate dissolved in 2000 ml of ethanol and 2000 ml water). The SBD was injected into the irrigation system with four weekly applications at 25 gallons per minute in addition to the scheduled fertigation regimen. The translocation of active ingredient was discerned through an oral assay by humans (i.e., taste test) within 48 hours following treatment. Treated tree seedlings were embedded into an untreated tree plantation within a deer management area. This allowed free movement of the deer and unobstructed browsing. Following deployment of the tree seedlings, the plantation was monitored for incidence of browse. Browsing on treated seedlings was completely controlled for the first growing season. To ensure control in subsequent years, additional SBD can be applied directly to the soil at the base of the seedling until the trees have grown above the height of browse.

Example 2

Systemic Biological Control

Crops can be conditioned and protected to be resistant and defensive to pathogens through the induction and translocation of specific, active substances through the present delivery system. Acquired resistance through systemic delivery can be effective against fungal, viral and insect pathogens without genetic modification of the crop. Based on the active substances induced, systemic conditioning and crop protection can be achieved.

Plant extractives and natural derivatives are used as deterrents and repellants. Some are also toxic to insect pests. Examples include Pyrethrum, Azadirachtin/neem, essential oils, and nicotine.

Systemic Acquired Resistance (SAR) compounds (sometimes referred to as pathogenesis related [PR] proteins) are used for insect and disease control. Examples include proteins and amino acids exhibiting anti-viral and anti-fungal effects.

Insect Growth Regulators (IGR) inhibit, interrupt or interfere with the metamorphosis of insect pest and/or the synthesis of chitin (exoskeleton), resulting in population control and death. They are also sometimes referred to as ecdysone or juvenile hormone mimics. Examples include Methoprene, Hydroprene, Nylar, Kinoprene.

Pheromones (sometime referred to as neuroendocrine response alkaloids) are designed to disorient insects and prevent mating, resulting in population control. An example is Hydroxydanaidal.

What is claimed is:

1. A systemic plant conditioning composition for conditioning a target plant that has an osmotic membrane comprising (a) between about 0.01 to 10% of a browse deterrent agent comprising denatonium benzoate, (b) about 0.01 to 10% of an osmolyte carrier composition comprising DMSO and betaine, (c) ammonium lauryl sulfate (ALS), and (d) a chelating agent, wherein the browse deterrent is exogenous.

2. The composition of claim 1, wherein the browse deterrent further comprises capsaicin, putramine or proven antifeedants, aversion or feed refusal agents singularly or in combination.

3. The composition of claim 2, wherein the feed refusal agent is vomitoxin.

4. The composition of claim 1, wherein the chelating agent is EDTA.

5. The composition of claim 1, wherein the betaine is glycine betaine.

6. The composition of claim 1, further comprising a solubilizing agent that will not burn the plant.

7. The composition of claim 6, wherein the solubilizing agent is ethanol or methanol.

8. A delivery system comprising (a) about 0.01 to 10% of an osmolyte carrier composition comprising DMSO and betaine; (b) between about 0.01 to 10% of a browse deterrent comprising capsaicin; (c) ammonium lauryl sulfate (ALS); and (d) a chelating agent.

9. The delivery system of claim 8, wherein the chelating agent is EDTA.

10. The delivery system of claim 8, wherein the betaine is glycine betaine.

11. The delivery system of claim 8, further comprising a solubilizing agent that will not burn the plant.

12. The delivery system of claim 11, wherein the solubilizing agent is ethanol or methanol.

13. The delivery system of claim 8, wherein the browse deterrent provides systemic resistance to a pest or pathogen.

14. The delivery system of claim 8, wherein the browse deterrent to osmolyte ratio is within the range of 10 ppm up to 1000 ppm.

15. The delivery system of claim 8, wherein the osmolyte carrier composition comprises three solutes.

16. The delivery system of claim 8, wherein the conditioning composition is formulated into a sustained release substance, which may include an encapsulated granule/prill or micro-encapsulated spheroid.

17. The delivery system of claim 16, wherein the conditioning composition is formulated to provide sustained release of the browse deterrent for a prescribed duration.

18. The delivery system of claim 17, wherein the prescribed duration is thirty, sixty, ninety, one hundred twenty, or one hundred eighty days.

19. The delivery system of claim 8, wherein the conditioning composition is formulated into a crystal, granule, liquid, solid, peat, organic fiber, prill, bead, soil additive, polymer, acrylamide, zeolite, silica, and/or clay.

20. A method of administering the delivery system of claim 8 to a target plant, comprising delivering the composition to soil surrounding the roots of the plant.

21. The method of claim 20, wherein the delivery system is not injected into the plant.

22. The method of claim 20, wherein the delivery system is not topically administered to the plant.

23. The method of claim 20, wherein at least one osmolyte carrier composition conditions the osmotic membrane in the target plant for enhanced root uptake and translocation.

24. The method of claim 20, wherein the delivery system is formulated to provide sustained release of the browse deterrent for a prescribed duration.

25. The method of claim 24, wherein the prescribed duration is thirty, sixty, ninety, one hundred twenty, or one hundred eighty days.

* * * * *

UNITED STATES PATENT AND TRADEMARK OFFICE

CERTIFICATE OF CORRECTION

PATENT NO. : 8,492,312 B2
APPLICATION NO. : 11/595464
DATED : July 23, 2013
INVENTOR(S) : Thomas E. Levar It is certified that error appears in the above-identified patent and that said Letters Patent is hereby corrected as shown below:

On the title page of the patent, item (12),

Under United States Patent:
Thomas

Should read:
Levar

On the title page of the patent, item (75),

Replace Inventor name:
Levar E. Thomas

With:
Thomas E. Levar

On the title page of the patent, item (73),

Replace Assignee name:
Regents of the University of Minnestoa

With:
Regents of the University of Minnesota

Signed and Sealed this
Twenty-ninth Day of October, 2013

Teresa Stanek Rea
*Deputy Director of the United States Patent and Trademark Office*